United States Patent
Tajima

(10) Patent No.: US 9,320,482 B2
(45) Date of Patent: Apr. 26, 2016

(54) RADIATION IMAGING SYSTEM AND RADIATION IMAGE DETECTOR

(71) Applicant: FUJIFILM Corporation, Tokyo (JP)

(72) Inventor: Takashi Tajima, Ashigarakami-gun (JP)

(73) Assignee: FUJIFILM CORPORATION, Tokyo (JP)

( * ) Notice: Subject to any disclaimer, the term of this patent is extended or adjusted under 35 U.S.C. 154(b) by 471 days.

(21) Appl. No.: 13/800,924

(22) Filed: Mar. 13, 2013

(65) Prior Publication Data
US 2013/0259196 A1    Oct. 3, 2013

(30) Foreign Application Priority Data

Mar. 27, 2012    (JP) ................ 2012-070573

(51) Int. Cl.
| | | |
|---|---|---|
| *G01T 7/00* | (2006.01) | |
| *A61B 6/00* | (2006.01) | |
| *G03B 42/02* | (2006.01) | |

(52) U.S. Cl.
CPC ............ *A61B 6/42* (2013.01); *A61B 6/4233* (2013.01); *A61B 6/4283* (2013.01); *A61B 6/465* (2013.01); *G01T 7/00* (2013.01); *G03B 42/02* (2013.01)

(58) Field of Classification Search
CPC ...... A61B 6/42; A61B 6/4233; A61B 6/4283; A61B 6/465; A61B 6/542; A61B 6/5294; A61B 6/545; G01T 7/00; G03B 42/02; G06F 19/3406; H05G 1/46
See application file for complete search history.

(56) References Cited

U.S. PATENT DOCUMENTS

| | | | |
|---|---|---|---|
| 2004/0071263 A1 | 4/2004 | Motoki | |
| 2005/0063512 A1* | 3/2005 | Maschke | 378/91 |
| 2006/0118727 A1* | 6/2006 | Tsuchino | 250/361 R |
| 2007/0165783 A1* | 7/2007 | Abu Tabanjeh | 378/116 |
| 2008/0292062 A1* | 11/2008 | Marar | G03B 42/02 378/207 |
| 2009/0086911 A1* | 4/2009 | Venugopal et al. | 378/96 |
| 2010/0104065 A1 | 4/2010 | Eguchi | |

FOREIGN PATENT DOCUMENTS

| | | |
|---|---|---|
| JP | 2000-350718 A | 12/2000 |
| JP | 2010-57707 A | 3/2010 |
| JP | 2012-11207 A | 1/2012 |
| WO | WO 2008/111355 A1 | 9/2008 |

OTHER PUBLICATIONS

Japanese Office Action for corresponding Japanese Application No. 2012-070573 dated Apr. 2, 2014 (with English translation).

* cited by examiner

*Primary Examiner* — David J Makiya
*Assistant Examiner* — John Corbett
(74) *Attorney, Agent, or Firm* — Birch, Stewart, Kolasch & Birch, LLP

(57) ABSTRACT

An X-ray imaging system has two types of electronic cassettes and one type of IP cassette. Upon entering a body portion to be imaged, an input and output controller retrieves from an imaging condition table of the IP cassette an imaging condition corresponding to the body portion as a reference imaging condition. An imaging condition calculator multiplies reference exposure time of the reference imaging condition by a sensitivity coefficient of each electronic cassette, to calculate an imaging condition to be applied in using each electronic cassette. An input and output controller displays the imaging conditions of the electronic cassettes and the IP cassette and choice buttons for choosing one of the electronic cassettes and the IP cassette in a list form on a monitor.

14 Claims, 6 Drawing Sheets

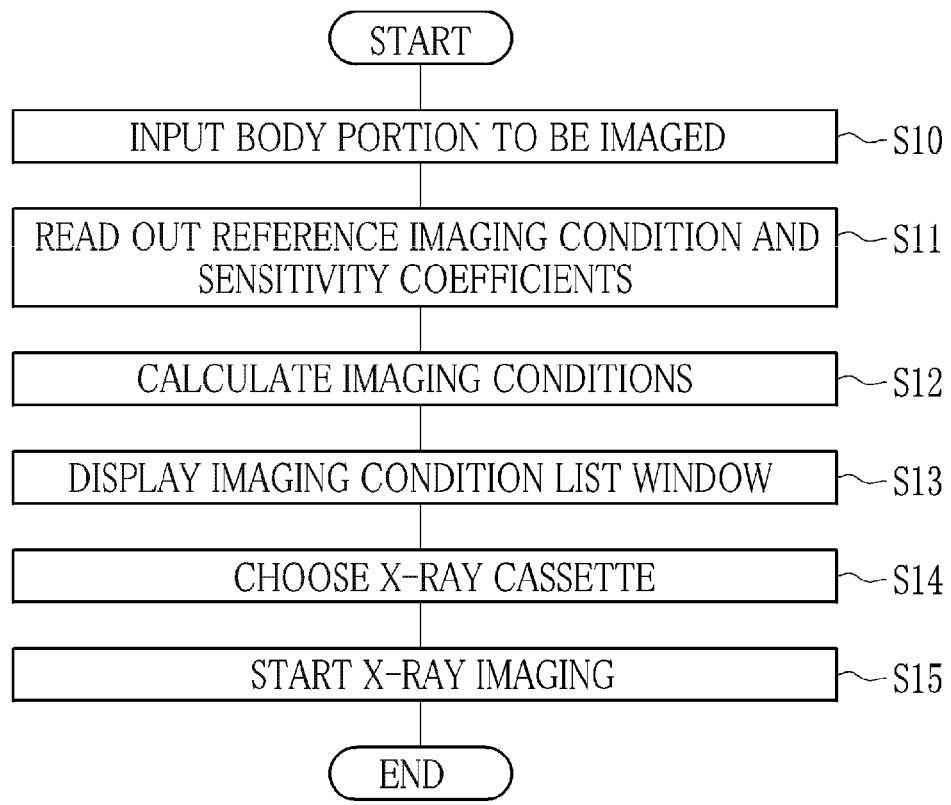
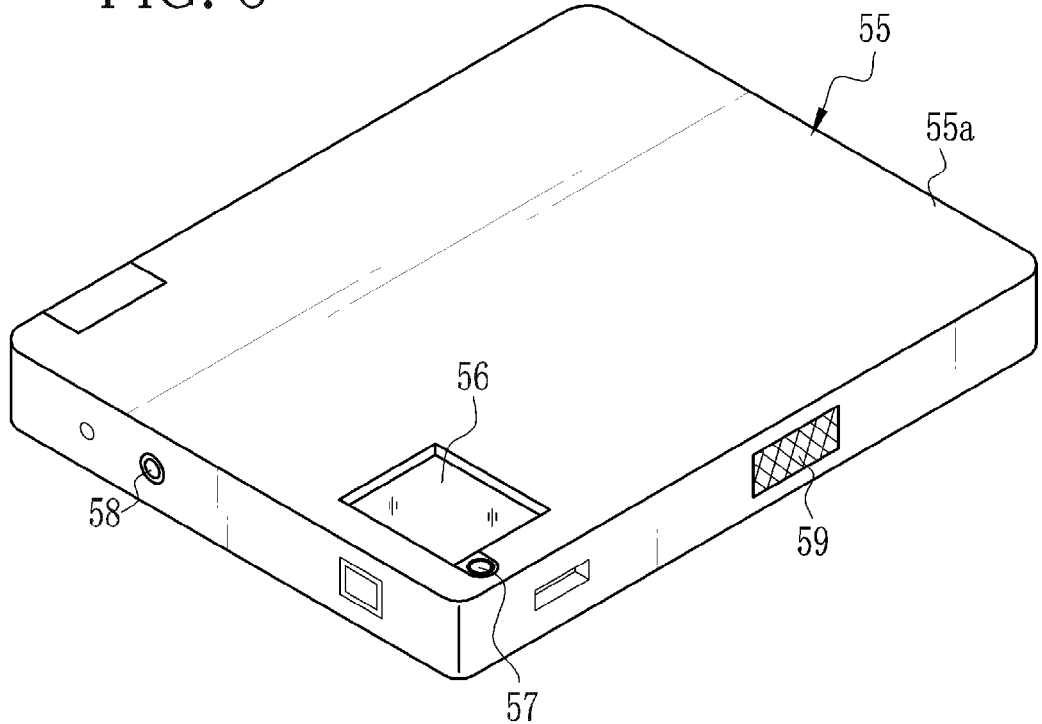

FIG. 9

| | AEC | TUBE CURRENT (mA) | EXPOSURE TIME (msec) |
|---|---|---|---|
| SET CONDITION | ON | 100 | 50 |
| | OFF | 100 | 40 |
| ACTUAL | ON | 100 | 40 |

CONFIRM

RADIATION IMAGING SYSTEM AND RADIATION IMAGE DETECTOR

BACKGROUND OF THE INVENTION

1. Field of the Invention

The present invention relates to a radiation imaging system and a radiation image detector.

2. Description Related to the Prior Art

In a medical field, a radiation imaging system, for example, an X-ray imaging system using X-rays is widely known. The X-ray imaging system is constituted of an X-ray source for applying X-rays to an object (patient), an X-ray image recorder or detector for recording or detecting an X-ray image produced from the X-rays passed through the object, a source controller for controlling the operation of the X-ray source, a console for controlling the operation of the X-ray image detector, and an emission switch for inputting an emission start command of the X-rays.

In the X-ray image recorder, an X-ray film is used as a recording material. In the X-ray image detector, an imaging plate (IP) or a flat panel detector (FPD) is used as a detection panel. The IP has a base coated with an optically stimulated phosphor, which accumulates X-ray energy. The FPD has a matrix of pixels each of which accumulates signal charge in accordance with an X-ray dose received therein. The FPD accumulates the signal charge on a pixel-by-pixel basis, and converts the accumulated signal charge into a voltage signal in its signal processing circuit. Thus, the FPD detects the X-ray image of the object, and outputs the X-ray image in the form of digital image data.

The X-ray film or the IP is contained in a flat rectangular cassette body of a standardized size, and is used as a film cassette or an IP cassette, respectively. Likewise, an electronic cassette (portable X-ray image detector) that has the FPD contained in the cassette body is also in practical use. The electronic cassette is loaded not only in a specific imaging stand but also in an existing imaging stand designed for the film cassette and the IP cassette. Furthermore, the electronic cassette can be used while being put on a bed or held by the patient himself/herself, to perform imaging of a body portion that is hard to take in the imaging stand. The electronic cassette is sometimes brought out from a hospital for use in bedside radiography of a home-care patient or in an outside accident or natural disaster site in case of emergency.

A plurality of electronic cassettes are generally prepared in the hospital in consideration of the number of imaging stands, a backup, and the like. When performing imaging, one of the electronic cassettes is chosen appropriately. It is also often the case that an old electronic cassette is still used after the purchase of a new electronic cassette. Some doctors preferably use the film cassette or the IP cassette that was included in the imaging stand.

The development of the X-ray image detector has been made in order of the film cassette, the IP cassette, and the electronic cassette. The sensitivity of the detector is increased with the progress of the development, and the electronic cassette can detect a sharp X-ray image from a low dose of X-rays. Even among the cassettes of the same type, there is difference in the sensitivity and the like depending on the type of the X-ray film, the structure of the IP, or the structure of the FPD. Thus, an imaging condition has to be set optimally in accordance with the sensitivity and the like of the cassette to be used.

Japanese Patent Laid-Open Publication No. 2012-011207 discloses an X-ray imaging system in which an imaging controller receives information about sensitivity and the like from an X-ray image detector (X-ray sensor unit). An imaging condition including tube voltage, tube current, and a mAs value is automatically set based on the received information, and is displayed on a monitor. US Patent Application Publication No. 2004/0071263 discloses an X-ray imaging system in which the operating status of a plurality of X-ray image detectors is displayed on a monitor of a console.

To meet demands for higher sensitivity of the X-ray image detector, lower radiation exposure, and the like, it is required of a medical facility to perform X-ray imaging with as low a dose as possible. According to the Japanese Patent Laid-Open Publication No. 2012-011207, the display of the imaging condition is switched concurrently with a change of the X-ray image detector, so it cannot be judged that whether or not the chosen X-ray image detector is more suitable for low-dose imaging than the others. Also, when the X-ray image detector is replaced with a new one, a change of the displayed imaging condition may confuse a radiological technician.

SUMMARY OF THE INVENTION

A main object of the present invention is to provide a radiation imaging system in which one of a plurality of radiation image detectors suitable for low-dose imaging is chosen with reliability.

Another object of the present invention is to provide the radiation imaging system and the radiation image detectors in which the appropriateness of an imaging condition can be easily confirmed.

To achieve the above and other objects of the present inventions, a radiation imaging system includes a radiation source, a plurality of types of radiation image detectors to be selectively used, and a monitor. The radiation source emits radiation to an object. Each of the radiation image detectors detects a radiation image based on the radiation passed through the object. The monitor displays a plurality of imaging conditions corresponding to the types of radiation image detectors in a comparable manner. Each of the imaging conditions includes at least tube current and exposure time of the radiation source.

The radiation image detector is a radiation cassette detachably loaded in an imaging stand. The radiation cassette has a detection panel for detecting the radiation image and a portable cassette body containing the detection panel. The radiation imaging system preferably further includes an information obtaining unit and an imaging condition calculator. The information obtaining unit obtains sensitivity information of each type of radiation cassette. The imaging condition calculator calculates based on the sensitivity information the imaging condition to be applied in selectively using each of the radiation cassettes.

The sensitivity information is preferably a sensitivity coefficient standardized with respect to the sensitivity of a reference radiation cassette being one of the plurality of radiation cassettes. The imaging condition calculator preferably calculates the imaging condition based on a reference imaging condition being the imaging condition of the reference radiation cassette and the sensitivity coefficient. The imaging condition calculator preferably calculates the exposure time by multiplying reference exposure time being the exposure time of the reference imaging condition by the sensitivity coefficient.

When a tube current-time product being the product of a calculation result of the exposure time and the tube current is out of a settable range of the radiation source, the imaging condition calculator preferably sets the exposure time such that the tube current-time product falls within the settable range.

When the calculation result of the exposure time is a minimum value settable in the radiation source or less, the imaging condition calculator preferably sets the exposure time at the minimum value and decreases the tube current.

The monitor preferably displays the reference imaging condition together with the plurality of imaging conditions.

The radiation imaging system may further include a storage device for storing the reference imaging condition and the imaging conditions calculated in the imaging condition calculator.

The reference radiation cassette may have the lowest sensitivity among the plurality of types of radiation cassettes.

When the selectively used radiation cassette has an automatic exposure control function, the monitor may display a set imaging condition to be applied in activating the automatic exposure control function, a calculated imaging condition to be applied in inactivating the automatic exposure control function, and an actual imaging condition in a comparable manner. The set imaging condition has a maximum value of the exposure time settable in the radiation source. The calculated imaging condition is the imaging condition calculated in the imaging condition calculator. The actual imaging condition has actual measurement values of the tube current and the exposure time.

The monitor may display a GUI together with the plurality of imaging conditions in order to choose a desired one of the plurality of types of radiation cassettes. The monitor may display the imaging condition of the radiation cassette chosen in the GUI distinguishably from the imaging conditions of the other radiation cassettes.

A radiation image detector according to the present invention is to be used selectively out of a plurality of types of radiation image detectors. The radiation image detector includes a detection panel for detecting a radiation image and a first screen for displaying a plurality of imaging conditions in a comparable manner. Each imaging condition includes at least tube current and exposure time to be applied in using each type of radiation image detector.

The radiation image detector is an electronic cassette that includes the detection panel having an arrangement of pixels for accumulating electric charge in accordance with a radiation dose and a portable cassette body containing the detection panel.

The radiation image detector may further include a second screen for displaying that the radiation image detector is chosen.

According to the present invention, the imaging conditions, each including at least the tube current and the exposure time, corresponding to the plurality of types of the radiation image detectors or recorders are displayed in a comparable manner. Thus, it is possible to reliably choose one of the radiation image detectors or recorders suitable for low-dose imaging, and easily confirm the appropriateness of the imaging conditions.

BRIEF DESCRIPTION OF THE DRAWINGS

For more complete understanding of the present invention, and the advantage thereof, reference is now made to the subsequent descriptions taken in conjunction with the accompanying drawings, in which:

FIG. 7 is a flowchart of operation before the start of X-ray imaging;

FIG. 8 is a perspective view of an electronic cassette having a liquid crystal display; and FIG. 9 is a plan view of an AEC confirmation window.

DESCRIPTION OF THE PREFERRED EMBODIMENTS

Figure 1:
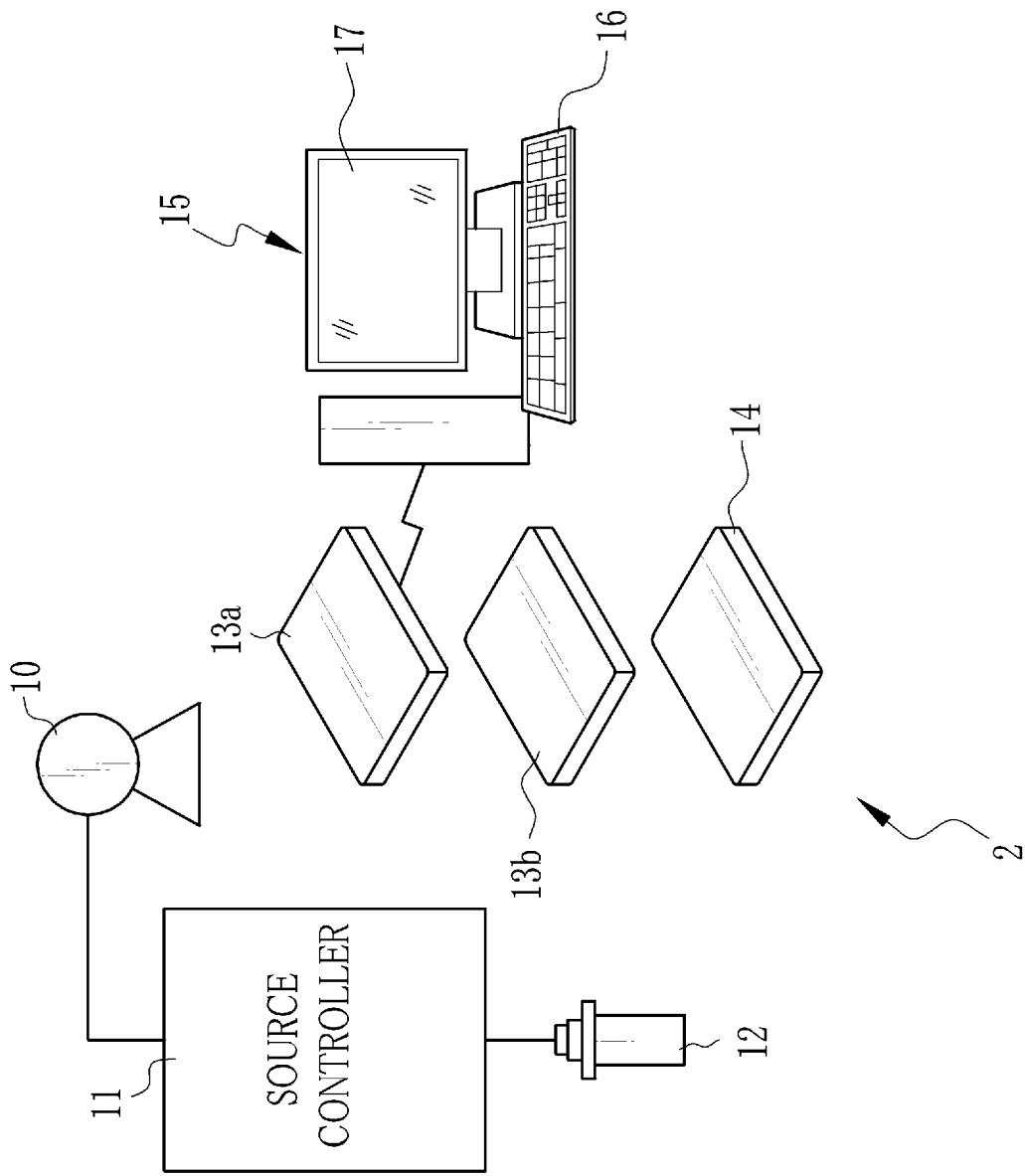
FIG. 1 is a schematic view showing the structure of an X-ray imaging system.

As shown in FIG. 1, an X-ray imaging system 2 is constituted of an X-ray source 10, a source controller 11, an emission switch 12, electronic cassettes 13a and 13b, an IP cassette (also called CR cassette) 14, and a console 15. The X-ray source 10 contains an X-ray tube for emitting X-rays. The source controller 11 controls the operation of the X-ray source 10. The emission switch 12 is used for commanding the source controller 11 to start emitting the X-rays from the X-ray source 10. Each of the electronic cassettes 13a and 13b and the IP cassette 14 detects an X-ray image of a patient's body portion. After the detection of the X-ray image, the electronic cassette 13a, 13b outputs X-ray image data under control of the console 15. The IP cassette 14 is set in an image reader (not shown) to optically read out the X-ray image recorded in an imaging plate. The console 15 takes charge of processing the X-ray image. Electronic cassettes, IP cassettes, film cassettes, and the like are generically called "X-ray cassettes". The X-ray cassette takes an arbitrary form as long as it is selectively loadable into an imaging stand or an imaging table. One of the X-ray cassettes is chosen in accordance with an imaging purpose, and is used while being loaded into the imaging stand or the imaging table (neither is shown). The X-ray source 10 is provided in a source shift mechanism (not shown), which sets the X-ray source 10 in a desired direction and a desired position.

The source controller 11 starts supplying electric power to the X-ray source 10 in response to an operation signal from the emission switch 12, so the X-ray source 10 starts emitting the X-rays. When exposure time that is determined based on an imaging condition has elapsed since the start of emission, the source controller 11 stops the electric power supply to the X-ray source 10 to stop the emission.

As is widely known, the electronic cassette 13a, 13b is constituted of an FPD and a portable cassette body. The IP cassette 14 has an imaging plate contained in an openable cassette body. The FPD and the imaging plate correspond to X-ray image detectors. The two electronic cassettes 13a and 13b have different specifications, and for example, the electronic cassette 13a has higher X-ray sensitivity than that of the electronic cassette 13b. The IP cassette 14 has lower X-ray sensitivity than that of the electronic cassettes 13a and 13b. Therefore, if the X-rays are produced by application of the same tube voltage and the same tube current to the X-ray tube of the X-ray source 10, the electronic cassette 13a has the shortest exposure time and the IP cassette 14 has the longest exposure time to obtain the X-ray image of the same image quality. The console 15 chooses one of the X-ray cassettes to be used. In FIG. 1, the electronic cassette 13a is chosen and connected to the console 15.

The electronic cassette 13a, 13b has the function of judging the start and stop of emission of the X-rays from the presence or absence of the X-rays incident thereon. When the start of emission is judged, the FPD starts a charge accumulation operation.

When the stop of emission is judged, the FPD turns a readout operation.

The console 15 is communicatably connected to the electronic cassettes 13a and 13b and the image reader (not shown) of the IP cassette 14 wiredly or wirelessly, and controls the operation of the electronic cassettes 13a and 13b and the image reader in response to an input operation by a radiological technician from an input device 16. The X-ray image transmitted from the electronic cassette 13a, 13b or the image reader is displayed on a monitor 17 of the console 15. Data for the X-ray image is written to a memory 21 or a storage device 22 (both shown in FIG. 2) of the console 15, or data storage such as an image server connected to the console 15 through a network. The input device 16 includes a keyboard and a mouse, a touch panel integrated with the monitor 17, or the like. As is widely known, the image reader opens the cassette body and exposes the imaging plate contained therein, upon the insertion of the IP cassette 14 into an insertion slot. By scanning the imaging plate that holds X-ray energy with a laser beam, light is emitted in accordance with the X-ray energy. The emitted light is measured to read the X-ray image.

The console 15 receives the entry of an examination order, which includes information about the sex and age of the patient, the body portion to be imaged, an imaging direction, and an examination purpose, and displays the examination order on the monitor 17. The examination order is inputted from an external system e.g. a HIS (hospital information system) for managing patient data or a RIS (radiography information system) for managing radiographic examination data, or inputted manually by the radiological technician. The body portion includes head, chest, abdomen, and the like. The imaging direction includes anterior, medial, diagonal, PA (X-rays are applied from a posterior direction), AP (X-rays are applied from an anterior direction), and the like. Note that, "the body portion" includes the body portion and the imaging direction in description below. The radiological technician checks the contents of the examination order on the monitor 17, and inputs the body portion on an operation screen displayed on the monitor 17 in accordance with the contents of the examination order.

Figure 2:
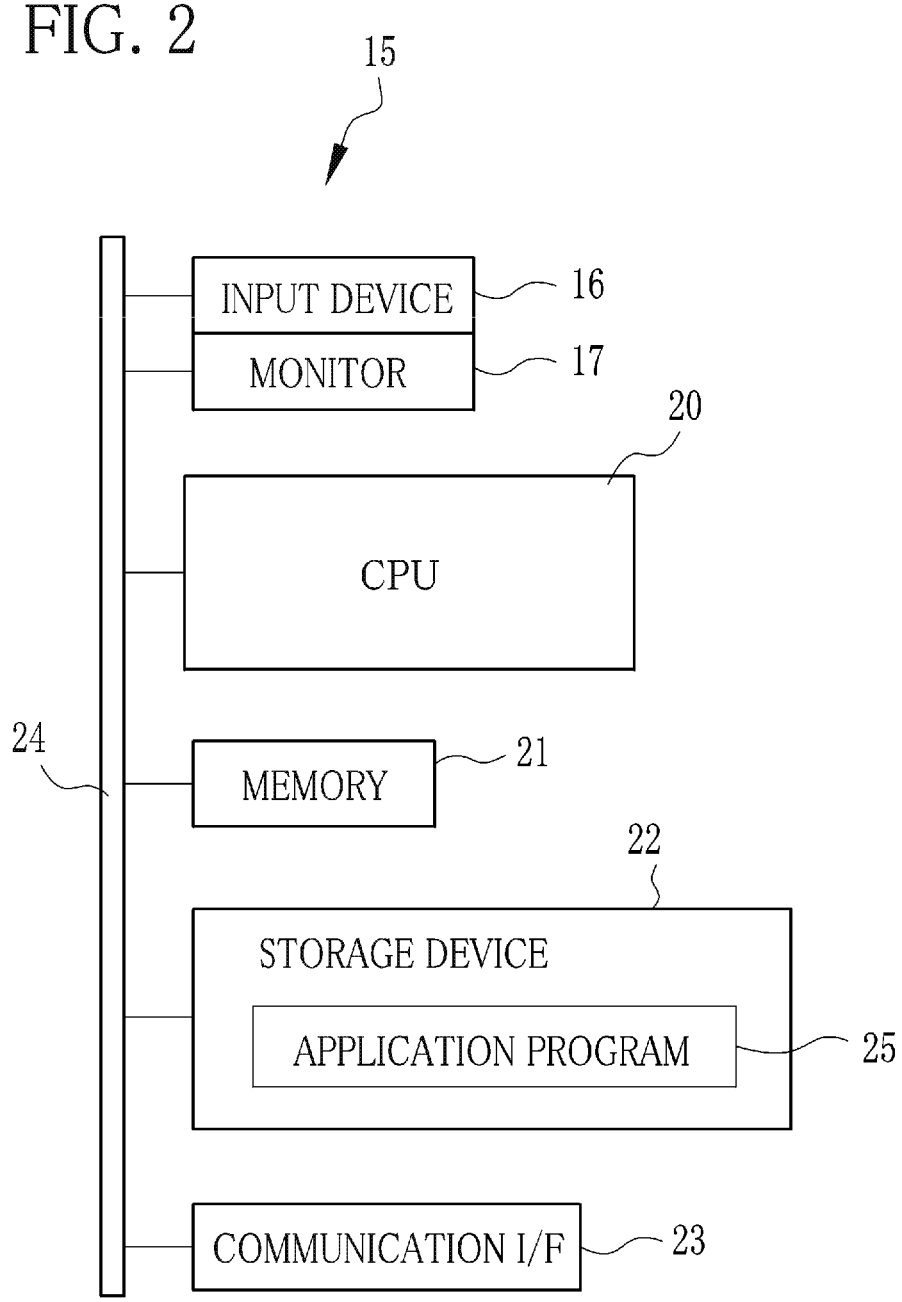
FIG. 2 is a block diagram of a computer that constitutes a console.

As shown in FIG. 2, the console 15 is composed of a computer having a CPU 20, the memory 21, the storage device 22, and a communication I/F 23, in addition to the input device 16 and the monitor 17 described above. These components are connected to each other via a data bus 24.

As the storage device 22, a hard disk drive is used, for example. The storage device 22 stores a control program and an application program 25. The application program 25 is a program that makes the console 15 perform various functions related to X-ray imaging, such as display processing of the examination order and the X-ray image, image processing of the X-ray image, and a setup of the imaging condition.

The memory 21 is used as a work memory with which the CPU 20 executes. The CPU 20 loads the control program stored on the storage device 22 into the memory 21, and runs the program for centralized control of the computer. The communication I/F (network interface) 23 controls data transmission from/to external devices including the RIS, the HIS, the image server, the electronic cassettes 13a and 13b, and the image reader. The storage device 22 of the console 15 stores an imaging condition table 30 shown in FIG. 3 and a sensitivity coefficient table 35 shown in FIG. 4.

Figure 3:
FIG. 3 is a table of a reference imaging condition.

In FIG. 3, the imaging condition table 30 stores reference imaging conditions, each including the tube voltage and tube current of the X-ray source 10 and the exposure time (reference exposure time) of the X-rays, that are determined in accordance with the body portion. The reference imaging conditions stored in the imaging condition table 30 are for use in the IP cassette (reference X-ray cassette) 14, which has the lowest X-ray sensitivity out of the electronic cassettes 13a and 13b and the IP cassette 14. The imaging condition table 30 is stored in advance on the storage device 22 (in a case where the IP cassette 14 and the console 15 was purchased together), or downloaded from the outside through the communication I/F 23.

Figure 4:
FIG. 4 is a table of a sensitivity coefficient.

In FIG. 4, the sensitivity coefficient table 35 stores DQE (detective quantum efficiency) of each of the electronic cassettes 13a and 13b and the IP cassette 14, and a sensitivity coefficient into which the DQE is standardized with respect to the X-ray cassette having the lowest sensitivity. Since a maximum of the DQE is "1", the DQE of the IP cassette 14 (type of X-ray cassette: IP) is "0.25", which indicates the lowest sensitivity. The DQE of the electronic cassette 13b (type of X-ray cassette: DR2) is "0.5", and the DQE of the electronic cassette 13a (type of X-ray cassette: DR1) is "0.75", which indicates the highest sensitivity. The sensitivity coefficient is the reciprocal of a sensitivity ratio with respect to the IP cassette 14 having the lowest sensitivity. In this embodiment, the sensitivity coefficient of the IP cassette 14 is "1" being a standard. The sensitivity coefficient of the electronic cassette 13b is "½", and the sensitivity coefficient of the electronic cassette 13a is "⅓".

The information of the DQE is inputted in advance manually by the radiological technician from the input device 16. Alternatively, each X-ray cassette may have the information of the DQE in its memory, and the information of the DQE may be transmitted from the memory to the console 15 through the communication I/F 23 upon first connection of the X-ray cassette to the console 15. Furthermore, the information of the DQE may be downloaded through the network from a homepage that provides X-ray cassette product data being uploaded. The sensitivity coefficient is calculated based on the obtained DQE. Instead of the DQE, NEQ (noise equivalent quanta) or the sensitivity coefficient itself may be used. The X-ray cassettes may be identified by abbreviations, such as IP, DR1, and DR2 of this embodiment. The X-ray cassettes are identified by at least one of the type of the X-ray cassette, a production number, a model number, and a lot number.

Figure 5:
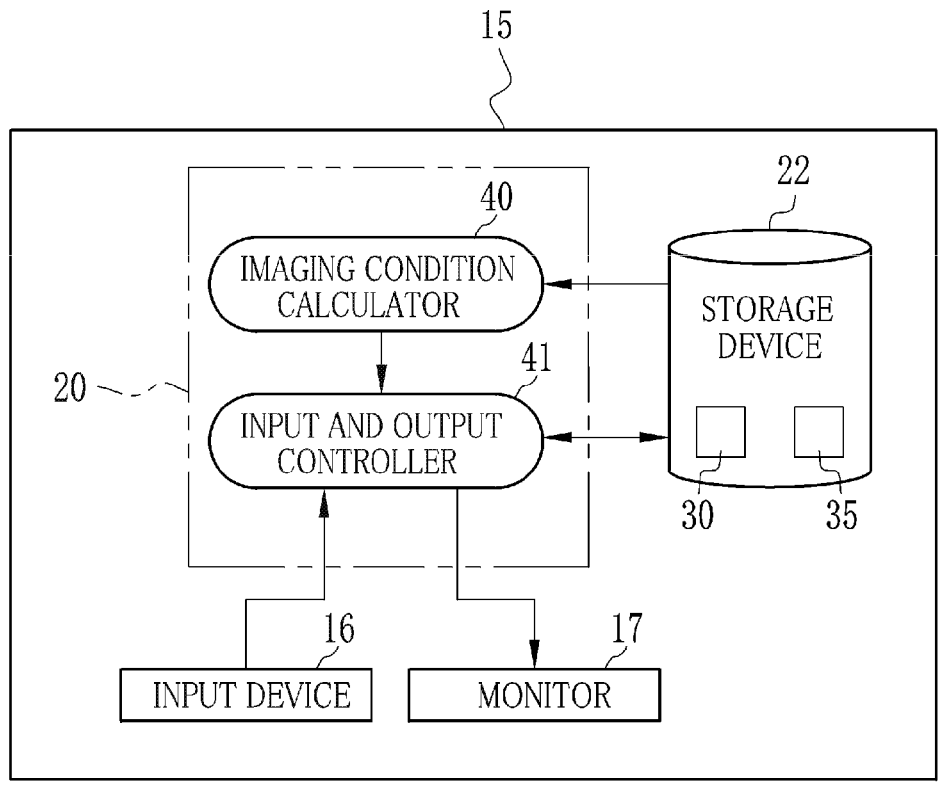
FIG. 5 is a block diagram of the console.

As shown in FIG. 5, in executing the application program 25, the CPU 20 of the console 15 functions as an imaging condition calculator 40 and an input and output controller 41. The imaging condition calculator 40 corrects the reference imaging condition, which is stored in the imaging condition table 30 for use in the IP cassette 14, to the imaging condition of the electronic cassette 13a or 13b based on the sensitivity coefficient of each X-ray cassette stored in the sensitivity coefficient table 35.

The input and output controller 41 retrieves the reference imaging condition that corresponds to the body portion inputted from the input device 16 from the imaging condition table 30 of the storage device 22. In this embodiment, if the body portion is "chest PA", a tube voltage of 130 kV, a tube current of 100 mA, and exposure time of 30 msec are retrieved. The input and output controller 41 retrieves the sensitivity coefficient of every X-ray cassette from the sensitivity coefficient table 35 of the storage device 22.

The imaging condition calculator 40 multiplies the reference exposure time of the reference imaging condition retrieved from the imaging condition table 30 by the sensitivity coefficient of each X-ray cassette. In this embodiment, if the body portion is the chest PA, the reference exposure time 30 msec is multiplied by "⅓" and "½". Thus, the exposure time of the electronic cassette 13a is 10 msec, and the exposure time of the electronic cassette 13b is 15 msec.

When a tube current-time product (mAs value) being the product of a calculation result of the exposure time and the tube current is a maximum value settable in the source controller 11 or more, or is a minimum value or less, the imaging condition controller 40 sets the exposure time such that the tube current-time product comes to the maximum or minimum value. Also, when the calculation result of the exposure time is a minimum value or less, the exposure time is set at the minimum value and the tube current is reduced. In addition to the exposure time and the tube current, the tube voltage may be corrected. However, correcting the tube voltage varies the radiation quality of the X-rays. Thus, the variation of the radiation quality at a certain tube voltage with varying the tube current and the exposure time is stored as information in the form of a table or a relational expression, and the tube current and the exposure time is further adjusted based on the information. It is preferable that only the exposure time is corrected basically, and the tube voltage and the tube current are corrected just in an unavoidable case.

The imaging condition calculator 40 transmits to the input and output controller 41 the reference imaging condition read out from the imaging condition table 30 and the information of the calculated imaging conditions.

The input and output controller 41 reads out screen data from the storage device 22 in accordance with an operation of the input device 16, and outputs various operation screens on the monitor 17 based on the read screen data. The input and output controller 41 receives an input of an operation command from the input device 16 through a GUI that is laid out in the operation screen.

Figure 6:
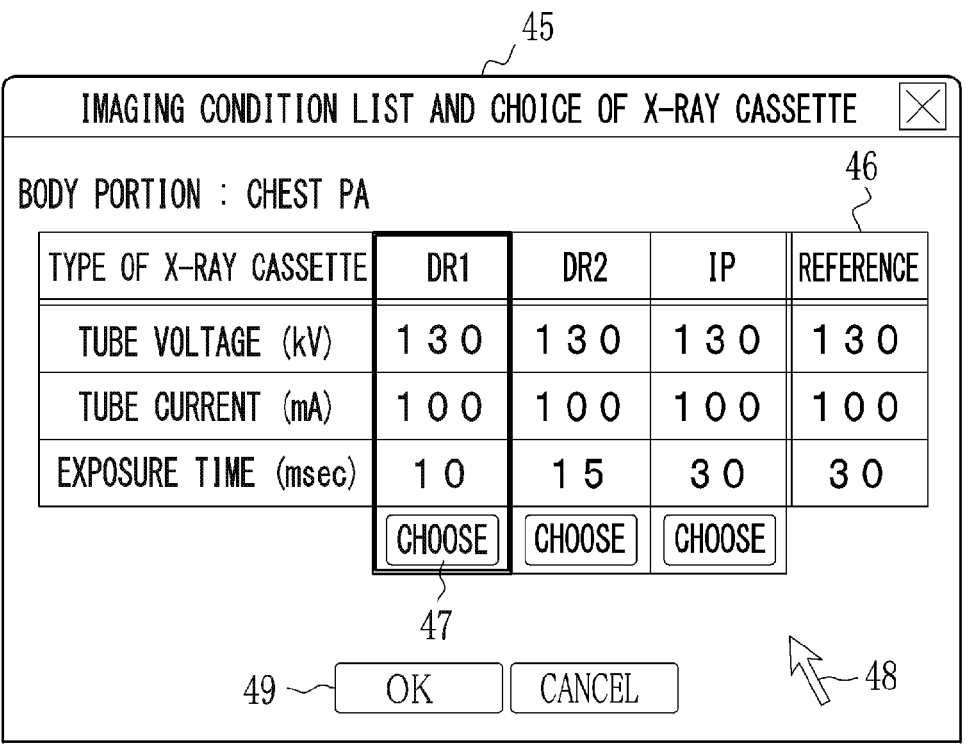
FIG. 6 is a plan view of an imaging condition list window.

After an input of the body portion, the input and output controller 41 displays on the monitor 17 an imaging condition list window 45 as shown in FIG. 6. The imaging condition list window 45 shows the information of the inputted body portion and a list of the imaging conditions, which includes the reference imaging condition for use in the IP cassette 14 (type of X-ray cassette: IP) read out from the imaging condition table 30 and the imaging conditions for use in the electronic cassettes 13a and 13b (type of X-ray cassette: DR1 and DR2, respectively) having the exposure time corrected by the imaging condition calculator 40. The list further shows the reference imaging condition in its rightmost column 46.

Each column that represents the imaging condition for use in the electronic cassette 13a, 13b, or the IP cassette 14 has a choose button 47 in its bottom. Only one out of the three choose buttons 47 can be chosen by a click of a cursor 48. The input and output controller 41 emphasizes the imaging condition chosen by the choose button 47 by enclosing with a bold line or changing color, as distinguished from the other imaging conditions. In FIG. 6, the electronic cassette 13a having the type of X-ray cassette of DR1 is chosen and its imaging condition is enclosed by the bold line.

After the choose button 47 of the desired X-ray cassette to be used in the X-ray imaging is chosen with the cursor 48, the radiological technician clicks an OK button 49 with the cursor 48. Thus, the choice of the X-ray cassette is completed. The radiological technician refers to the imaging condition of the chosen X-ray cassette, and manually enters the same imaging condition to the source controller 11.

Next, a procedure prior to the start of the X-ray imaging with the use of the X-ray imaging system 2 will be described with referring to a flowchart of FIG. 7. Prior to the X-ray imaging, the radiological technician enters the body portion to be imaged from the input device 16 in accordance with the examination order displayed on the monitor 17 (S10).

Then, the reference imaging condition corresponding to the body portion entered in S10 is read out from the imaging condition table 30 of the storage device 22, and the sensitivity coefficients of every X-ray cassette is read out from the sensitivity coefficient table 35 to the imaging condition calculator 40 (S11). The imaging condition calculator 40 multiplies the reference exposure time of the reference imaging condition by the sensitivity coefficient of each X-ray cassette, to calculate the imaging condition of each X-ray cassette (S12). The calculated imaging conditions are transmitted to the input and output controller 41 together with the imaging condition of the IP cassette 14.

Then, the input and output controller 41 displays the imaging condition list window 45 on the monitor 17 (S13). The radiological technician checks the imaging condition list window 45, and chooses the choose button 47 of the desired X-ray cassette, and clicks the OK button 49 (S14).

After that, the radiological technician makes the patient stand in a predetermined position in front of the imaging stand or lie down on the imaging table, and sets the X-ray cassette chosen in S14 in the imaging stand or table. The height and horizontal position of the X-ray cassette are adjusted so as to be aligned with the body portion of the patient. The height and horizontal position of the X-ray source 10 and the size of the irradiation field are adjusted in accordance with the position of the X-ray cassette and the size of the body portion. The same imaging condition as that displayed on the imaging condition list window 45 is set in the source controller 11, and the emission switch 12 is pressed to start the X-ray imaging (S15).

According to the present invention, as described above, the imaging conditions of the plurality of X-ray cassettes are displayed in a list form in a comparable manner. Therefore, the radiological technician can choose the X-ray cassette, while checking which X-ray cassette is suitable for low-dose imaging.

The radiological technician knows which X-ray cassette has high sensitivity to certain extent, but is not sure how much the use of the high sensitivity cassette reduces the X-ray dose as compared with the other X-ray cassettes. Also, since there are quite a number of imaging conditions, the radiological technician cannot remember all the imaging conditions. Furthermore, if only the imaging condition of a new X-ray cassette is displayed just after the purchase of the new X-ray cassette, the radiological technician may be confused at the difference in the imaging condition between an old X-ray cassette and the new one. According to the present invention, the imaging conditions of the plurality of X-ray cassettes are displayed in a list form, so the radiological technician can numerically grasp the difference in the performance among the X-ray cassettes. This prevents confusion for the radiological technician and allows easy choice of the X-ray cassette.

The imaging condition of each X-ray cassette is calculated with ease by multiplying the reference exposure time by the sensitivity coefficient. Thus, the imaging condition calculator is composed of a simple multiplier, and the calculation does not need much time. The shorter the exposure time is corrected, the less the X-ray image deteriorates by a body motion of the patient.

Since the reference imaging condition is displayed together with the imaging conditions of the X-ray cassettes, the radiological technician can easily judge the appropriateness of the calculated imaging conditions. Especially, since the imaging condition of the conventionally used X-ray cassette, such as the IP cassette, is displayed as the reference imaging condition, the radiological technician can check correctness in the values of the reference imaging condition. Also, by numerically checking the performance of the new X-ray cassette as compared with the performance of the old one, it is possible to choose the X-ray cassette with high reliability. Distinguishably displaying the imaging condition of the chosen X-ray cassette can prevent a cassette choice error.

In the above embodiment, the sensitivity coefficient table 35 is stored in the storage device 22, and the imaging condition calculator 40 calculates the imaging conditions based on the sensitivity coefficients whenever the X-ray imaging is performed.

Instead of this, the imaging condition calculator 40 may calculate the imaging conditions of each body portion for use in each X-ray cassette, when the DQEs or sensitivity coefficients are obtained from the input device 16 or through the communication I/F 23. The calculated imaging conditions may be stored in the storage device 22 with being associated with the types of cassettes. Storing the imaging conditions of every X-ray cassette may consume the capacity of the storage device 22, but eliminates the need for calculating the imaging conditions whenever performing the X-ray imaging.

The list of the imaging conditions is not necessarily displayed on the monitor of the console. The source controller may have the same structure as the imaging condition calculator, the input and output controller, the storage device for storing the imaging condition table and the sensitivity coefficient table, and the monitor, and the list of the imaging conditions may be displayed on a monitor of the source controller. In another case, as shown in FIG. 8, a cassette body 55a of an electronic cassette 55 is provided with a small liquid crystal display 56 and a button 57. The reference imaging condition and the information of the imaging conditions calculated by the imaging condition calculator may be transmitted from the console to the electronic cassette 55. The list of the imaging conditions may be displayed on the liquid crustal display 56 at a touch of the button 57. The cassette body 55a may be provided with an indicator such as an LED lump 58 and a speaker 59 at its side walls. The indicator may be actuated, when the electronic cassette 55 is chosen to be used. This prevents a setting error of the electronic cassette, for example, performing the X-ray imaging while forgetting about setting the electronic cassette in the imaging stand or table, or applying the X-rays to the electronic cassette set in the imaging table while choosing the electronic cassette set in the imaging stand.

Out of items of the imaging condition, the tube current and the exposure time are parameters related to the X-ray dose. Thus, at least the tube current and the exposure time are preferably displayed in the list. The imaging conditions of the X-ray cassettes may be displayed in turn, instead of in a list form.

In the above embodiment, the desired X-ray cassette is manually chosen in the list displayed on the monitor. However, the types of the X-ray cassettes connected to the console may be identified automatically, and one of the displayed imaging conditions may be chosen automatically.

If the electronic cassette has the function of automatic exposure control (AEC) by which the emission of the X-rays is stopped when an integral X-ray dose has reached a predetermined value, a maximum value of the exposure time is set in the source controller 11 in order to prevent a situation in which the emission is ended before the AEC judges the stop of the emission. Therefore, even if the electronic cassette having the AEC function has higher sensitivity than the other electronic cassettes, the exposure time of the electronic cassette having the AEC function is longer in the list than the other electronic cassettes. Displaying such a list may cause the radiological technician to feel incongruity, so the radiological technician is preferably notified of the presence or absence of the AEC function by providing an indication column in the list.

In the case of choosing the electronic cassette having the AEC function, even if the maximum value of the exposure time is set, the AEC stops the emission of the X-rays before a lapse of the set exposure time in actual fact. However, the radiological technician feels anxiety without having a way of checking whether the AEC function works or not. For this reason, after the completion of the X-ray imaging, an AEC confirmation window 65 shown in FIG. 9 is preferably displayed on the monitor 17 of the console 15.

The AEC confirmation window 65 has a row 66 of "set condition" and a row 67 of "actual". The row 66 has a row 66a representing the state of activating the AEC function ("AEC-ON") and a row 66b representing the state of inactivating the AEC function ("AEC-OFF"). The row 66a displays set tube current and set exposure time (maximum value) to be applied in activating the AEC function, which are displayed on the list of the imaging conditions. The row 66b displays calculated tube current and calculated exposure time to be applied in inactivating the AEC function, which are calculated by the imaging condition calculator 40 based on the sensitivity coefficient. The row 67 displays actual tube current and actual exposure time applied to the X-ray source 10 in actual X-ray imaging. The AEC confirmation window 65 is closed upon a click of a confirm button 68 with the cursor 48. To obtain the actual exposure time of the row 67, the source controller is provided with a timer, and a measurement result of the timer is transmitted from the source controller to the console after the completion of the X-ray imaging.

When the AEC function works, if the patient is thin, the actual exposure time is slightly less than the calculated exposure time. If the patient is fat, the actual exposure time is almost the same as the calculated exposure time, though is slightly more than the calculated exposure time. On the other hand, the AEC function does not work due to some failure, the actual exposure time is the same as the set exposure time. Therefore, the radiological technician can confirm whether the AEC function works or not by checking the AEC confirmation window 65.

The console and the electronic cassette are separate in the above embodiment, but the console is not necessarily independent. The electronic cassette may have the function of the console. Likewise, the source controller and the console may be integrated. A film cassette may be used in addition to or instead of the electronic cassettes and the IP cassette. In this case, a sensitivity coefficient table of the film cassette is prepared.

The FPD to be used as the X-ray image detector may be installed undetachably in the imaging stand. In this case, a plurality of imaging stands having the FPDs of different sensitivity are provided. The imaging conditions of each imaging stand are displayed in a comparable manner so as to choose a new one out of the imaging stands of the same type.

Furthermore, in addition to the plurality of imaging stands having the FPDs, at least one cassette type imaging stand and a plurality of X-ray cassettes may be prepared. The imaging conditions of each imaging stand and each X-ray cassette may be displayed on a comparable manner.

In the above embodiment, the tube current and the exposure time are displayed as the items of the imaging condition. Instead of or in addition to the tube current and the exposure time, a tube current-time product (mAs value) being the product of the tube current and the exposure time may be displayed. Instead of the exposure time, a result of multiplying the tube current-time product by the sensitivity coefficient may be displayed as the imaging condition of each X-ray cassette.

The present invention is applicable to a radiation imaging system using another type of radiation such as y-rays instead of the X-rays.

Although the present invention has been fully described by the way of the preferred embodiment thereof with reference to the accompanying drawings, various changes and modifications will be apparent to those having skill in this field. Therefore, unless otherwise these changes and modifications depart from the scope of the present invention, they should be construed as included therein.

What is claimed is:

1. A radiation imaging system comprising:
   an X-ray radiation source for emitting X-ray radiation to an object;
   a plurality of types of X-ray radiation image detectors to be selectively used, each of said X-ray radiation image detectors detecting an X-ray radiation image based. on said X-ray radiation passed through said object;
   a monitor for displaying a plurality of imaging conditions corresponding to said types of X-ray radiation image detectors in a comparable manner, each of said imaging conditions including at least tube current and exposure time of said X-ray radiation source;
   an information obtain unit for obtaining sensitivity information of each of said types of X-ray radiation image detectors, said sensitivity information including a sensitivity coefficient standardized with respect to sensitivity of a reference X-ray radiation image detector being one of said plurality of X-ray radiation image detectors; and
   an imaging condition calculator for calculating said imaging condition to be applied in selectively using each of said X-ray radiation image detectors based on said sensitivity coefficient and a reference imaging condition being said imaging condition of said reference X-ray radiation image detector.

2. The radiation imaging system according to claim 1, wherein said X-ray radiation image detector is an X-ray radiation cassette detachably loaded in an imaging stand, and said X-ray radiation cassette has a detection panel for detecting said X-ray radiation image and a portable cassette body containing said detection panel.

3. The radiation imaging system according to claim 2, wherein said monitor displays a GUI together with said plurality of imaging conditions in order to choose a desired one of said plurality of types of X-ray radiation cassettes.

4. The radiation imaging system according to claim 3, said monitor displays said imaging condition of said X-ray radiation cassette chosen in said GUI distinguishably from said imaging conditions of the other X-ray radiation cassettes.

5. The radiation imaging system according to claim 1, wherein said imaging condition calculator calculates said exposure time by multiplying reference exposure time being said exposure rime said reference imaging condition by said sensitivity coefficient.

6. The radiation imaging system according to claim 5. wherein when a tube current-time product being a product of a calculation result of said exposure time and said tube current is out of a settable range of said X-ray radiation source, said imaging condition calculator sets said exposure time such that said tube current-time product falls within said settable range.

7. The radiation imaging system according to claim 6, wherein her said calculation result of said exposure time is a minimum value settable in said X-ray radiation source or less, said imaging condition calculator sets said exposure time at said minimum value and decreases said tube current.

8. The radiation imaging system according to 1, wherein said monitor displays said reference imaging condition together with said plurality of imaging conditions.

9. The radiation imaging system according to claim 1, further comprising a storage device for storing said reference imaging condition and said imaging conditions calculated in said imaging condition calculator.

10. The radiation imaging system according to claim1, wherein said reference X-ray radiation image detector has lowest sensitivity among said plurality of types of X-ray radiation image detectors.

11. A radiation imaging system comprising;
   an X-ray radiation source for emitting radiation to an object:
   plurality of types of X-ray radiation image detectors to be selectively used, each of said X-ray radiation image detectors detecting an X-ray radiation image based an said X-ray radiation passed through said object;
   a monitor for dispiavins4 a plurality of imaging conditions corresponding to said type of X-ray radiation image detectors in a comparable manner, each of said imaging conditions including at least tube current a re time of said X-ray radiation source:
   an information obtaining unit for obtaining sensitivity information of each of said types of X-ray radiation image detectors; and
   an imagine condition calculator for calculating based on said sensitivity information said imaging condition to be applied in selectively using each of said X-ray radiation image detectors, wherein
   when said selectively used X-ray radiation image detector has an automatic exposure control function, said monitor displays a set imaging condition to be applied in activating said automatic exposure control function, a calculated imaging condition to be applied in inactivating said automatic exposure control function, and an actual imaging condition in a comparable manner, wherein said set imaging condition has a maximum value of said exposure time settable in said X-ray radiation source:
   said calculated imaging condition is said imaging condition calculated in said imaging; condition calculator; and
   said actual imaging condition has actual measurement values of said tube current and said exposure time.

12. A radiation image detector to be used out of a plurality of types et X-ray radiation image detectors, comprising:
   a detection panel for detecting an X-ray radiation image; and a first screen for displaying a plurality of imaging conditions of the plural type of X-ray radiation image detectors in a comparable manner, each of said imaging conditions including at feast tube current and exposure tune to be applied in using each of said plurality of types of X-ray radiation image detectors;
   a first screen for displaying a plurality of imaging conditions of the plural type of X-ray radiation image detectors in a comparable manner, each of said imaging conditions including at least tube current and exposure time to be applied in using each of said plurality of types of X-ray radiation image detectors;
   an information obtaining unit for obtaining sensitivity information of each of said types of X-ray radiation image detectors, said sensitivity of a reference including a sensitivity coefficient standardized with respect to sensitivity of a reference X-ray radiation image detector being one of said plurality of X-ray radiation image detectors; and an imaging condition calculator for calculating said imaging condition to be applied in selectively using each of said X-ray radiation image detectors based on said sensitivity coefficient and a reference imaging condition being said imaging condition of said reference X-ray radiation image detector.

13. The radiation image detector according to claim 12, being an electronic cassette that includes said detection panel having an arrangement of pixels for accumulating electric charge in accordance with a radiation dose and a portable cassette body containing said detection panel.

14. The radiation image detector according to claim 13, further comprising a second screen for displaying that said X-ray radiation image detector is chosen.

* * * * *